US00PP19879P2

(12) United States Plant Patent
Seabrook

(10) Patent No.: US PP19,879 P2
(45) Date of Patent: Mar. 31, 2009

(54) ***VERBENA* PLANT NAMED 'SEABROOK'S LAVENDER'**

(50) Latin Name: *Verbena×hybrida*
Varietal Denomination: Seabrook's Lavender

(76) Inventor: Peter Seabrook, 213 Beehive La., Chelmsford (GB), CM2 9SH ( * ) Notice: Subject to any disclaimer, the term of this patent is extended or adjusted under 35 U.S.C. 154(b) by 0 days.

(21) Appl. No.: 12/070,282

(22) Filed: Feb. 15, 2008

(51) Int. Cl.
*A01H 5/00* (2006.01)

(52) U.S. Cl. ..... Plt./308
(58) Field of Classification Search ..... Plt./308
See application file for complete search history.

*Primary Examiner*—Annette H. Para
*Assistant Examiner*—S. B McCormick Ewoldt

(57) ABSTRACT

A new and distinct cultivar of *Verbena* plant named 'Seabrook's Lavender' that is characterized by lavender colored flowers that have a long corolla and a strong fragrance.

1 Drawing Sheet

Botanical classification: *Verbena×hybrida.*
Variety denomination: 'Seabrook's Lavender'.

BACKGROUND OF THE INVENTION

The present invention relates to a new and distinct cultivar of *Verbena* plant botanically known as *Verbena×hybrida* and hereinafter referred to by the cultivar name 'Seabrook's Lavender'.

'Seabrook's Lavender' was discovered as a single plant growing in a bed of *Verbena* cultivars in a cultivated area of Chelmsford, Essex, England in 1996. The exact parent plants are unknown.

Asexual reproduction by softwood cuttings of the new cultivar 'Seabrook's Lavender' first occurred in 1998 in Chelmsford, Essex, England. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Verbena* cultivar 'Seabrook's Lavender'. These traits in combination distinguish 'Seabrook's Lavender' as a new and distinct cultivar apart from other known existing varieties of *Verbena.*

1. *Verbena* 'Seabrook's Lavender' exhibits a strong fragrance.
2. *Verbena* 'Seabrook's Lavender' exhibits lavender colored flowers.
3. *Verbena* 'Seabrook's Lavender' exhibits flowers that have a long corolla.

The closest comparison variety is *Verbena* 'La France' (not patented). 'Seabrook's Lavender' is different than 'La France' in having a longer corolla.

BRIEF DESCRIPTION OF THE DRAWING

The accompanying photograph illustrates the distinguishing traits of *Verbena* 'Seabrook's Lavender'. The plant in the photograph shows an overall view of a 12 week old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Verbena* cultivar named 'Seabrook's Lavender'. Data was collected in Cambridgeshire, England from 12 week old plants grown outdoors. The plants were grown in 23 cm diameter containers. The time of year was Summer and the daytime temperature ranged from 15 to 26° Centigrade. The temperature at night ranged from 12 to 21° Centigrade. No photoperiodic treatments were used. Color determinations are in accordance with The Royal Horticultural Society Colour Chart 2001 edition, except where general color terms of ordinary dictionary significance are used. The growing requirements are similar to the species.

'Seabrook's Lavender' has not been tested under all possible conditions and phenotypic differences may be observed with variations in environmental, climatic, and cultural conditions, however, without any variance in genotype.

Botanical classification: *Verbena×hybrida* cultivar 'Seabrook's Lavender'.
Sexuality: Hermaphrodite.
Designated use: Short-lived perennial for borders and containers.
Soil requirements: Requires reasonable winter drainage, otherwise tolerant.
Light requirements: Sun or semi-shade for optimum flowering.
Propagation method: Softwood cuttings.
Rooting habit: Fibrous.
Time required to develop roots on an initial cutting: 10–14 days.
Recommended air temp for cutting to develop roots: 18–21° C. (65–70° F.).
Is variety evergreen, semi-evergreen or deciduous: Semi-evergreen.
Dimensions of new variety at maturity: Height 400 mm, width 800 mm.
Time required for a rooted cutting to reach commercial size: 8–10 weeks.

Is the new variety vigorous (list percentage and standard): Taller and more vigorous than other vegetatively propagated varieties.
Habit of new variety: Initially semi-erect, later forming a flattened dome.
USDA hardiness zone: Zone 8.
Particular pests and diseases the new variety is susceptible to: No specific pests or diseases.
Branching habit: Branching freely.
Branch angle at emergence: Approximately 45°.
Branch color: Green 137C.
Branch shape: Square.
Branch approx length and diameter: Length to 450 mm; diameter 3 mm.
Branch surface: Moderately coarsely whitish pubescent, a few of the hairs tipped with purple glands.
Presence of lenticels on branch surface: Absent.
Internode length: 50 mm.
Leaf shape: Ovate, sometimes with two short lateral lobes.
Leaf length: 45 mm.
Leaf width: 28 mm.
Leaf arrangement: Decussate.
Leaf margins: Crenate.
Leaf division: Entire.
Leaf apex shape: Obtuse.
Leaf base shape: Obtuse, tending to truncate.
Leaf color of upper surface: Green 137A.
Leaf color of lower surface: Green 137B.
Leaf pubescence of upper surface: Minutely pubescent.
Leaf pubescence of lower surface: Finely pubescent, mainly on the veins.
Leaf venation pattern: Pinnate.
Leaf vein color (upper and lower): Upper: as lamina. Lower: Yellow-Green 146C.
Leaf fragrance: Absent.
Leaf attachment: Petiolate, petioles winged.
Petiole length: 13 mm.
Petiole width: 3 mm.
Petiole color: Green 137A.
Petiole pubescence: Moderately coarsely pubescent, a few of the hairs tipped with purple glands.
Stipules: Absent.
Flowering season: May–November.
Flower arrangement: Terminal inflorescences, flowers densely imbricate.
Inflorescence approximate number of flowers: 25.
Peduncle length: 55 mm.
Peduncle diameter: 2 mm.
Peduncle shape: Square.
Peduncle color: Green 137B.
Peduncle pubescence: Moderately pubescent, a few of the hairs tipped with purple glands.
Pedicels: Absent.
Flowers persistent or self-cleaning: Self-cleaning.
Flower type: Single.
Flower fragrance: Honeyed scent, strongest in the evening.
Bud shape: Tubular.
Bud length: 15 mm.
Bud diameter: 2 mm.
Bud: color: Purple-Violet N82A.
Flower aspect: Radiating from centre of inflorescence.
Calyx length: 12 mm.
Calyx diameter: 2 mm.
Calyx pubescence: Densely pubescent, some hairs tipped with purple glands.
Calyx color: Green 138B.
Sepal number: 5.
Sepal shape: Ovate-deltate, strongly folded inward along the midline.
Sepal apex: Acute.
Sepal margin: Entire.
Corolla shape: Salverform, limb set obliquely on tube.
Corolla number of lobes: 5.
Corolla segments fused or free: United into limb round the mouth of the tube.
Corolla greatest overall diameter: 16 mm.
Corolla length of tube: 20 mm.
Corolla lobe shape: Broad oval to round, the tip cleft to about ¼ the length of the lobe, lowest lobe slightly larger than the others, upper two united for about ⅓ of length.
Corolla lobe margin: Entire, shallowly undulate.
Corolla lobe surface: Smooth.
Corolla lobe length: Upper lobes: 6 mm, Lowest lobe: 5 mm.
Corolla lobe width: Upper lobes: 6 mm, Lowest lobe: 5 mm.
Corolla lobe color: Purple-Violet N80B, N80A around the mouth of the tube.
Stamens number: 4.
Filament length: 1 mm.
Filament width: 0.5 mm.
Filament: color: White 155A.
Anther length: 1 mm.
Anther width: 1 mm.
Anther shape: Ovoid with a short, spur-like appendage.
Anther color: Yellow-Green 150D.
Pollen color: Yellow 1D.
Pollen quantity: Moderate.
Pistil number: 1.
Stigma shape: Bifid, one lobe larger than the other.
Stigma dimensions: Length 1 mm, width 1 mm.
Stigma color: Green 138B.
Style shape: Hair-like.
Style dimensions: Length 16 mm, width 0.5 mm.
Style color: Green 138B.
Ovary shape: Ovoid with four longitudinal furrows.
Ovary inferior/superior: Superior.
Ovary dimensions: Length 1 mm, width 1 mm.
Ovary color: Green 143C.
Seed production: Seed production has not been observed.
Disease and pest resistance: Has not been observed.

It is claimed:

1. A new and distinct variety of *Verbena* plant named 'Seabrook's Lavender' as described and illustrated.

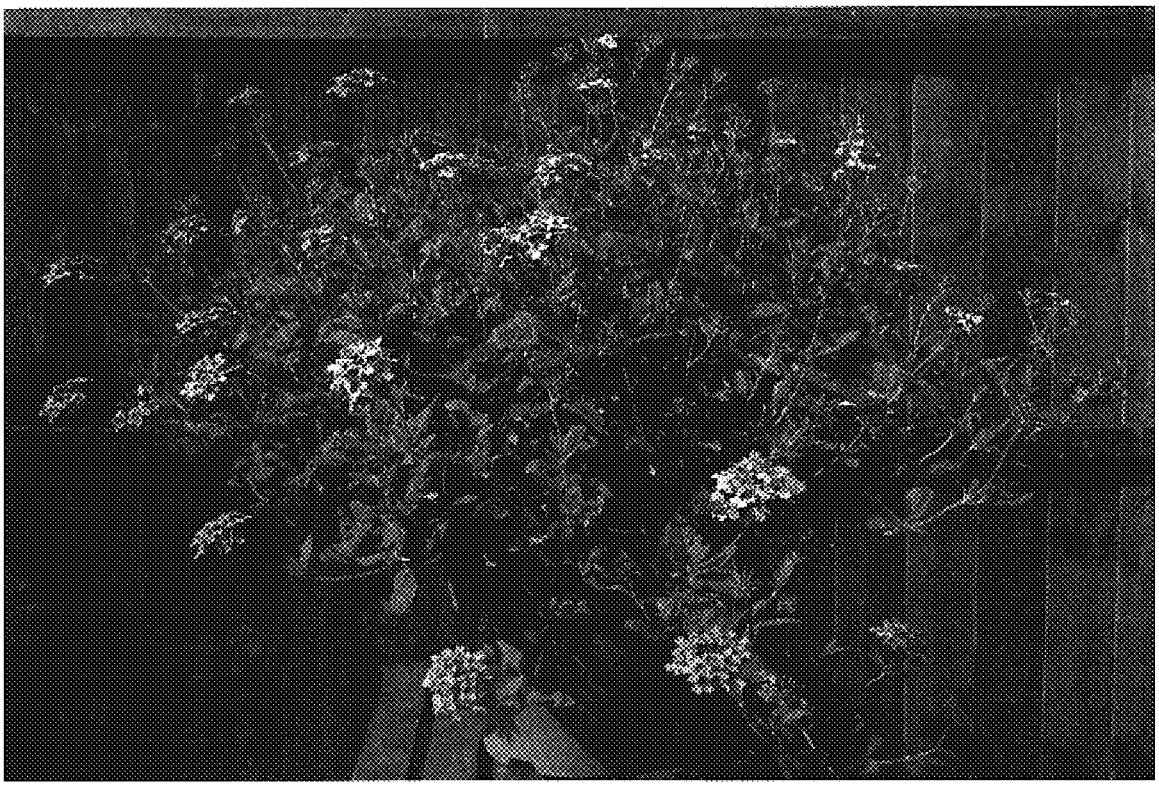

* * * * *